(12) United States Patent
Choe et al.

(10) Patent No.: US 8,644,943 B2
(45) Date of Patent: Feb. 4, 2014

(54) APPARATUS FOR STIMULATING LIVING BODY

(75) Inventors: Il Hwan Choe, Seoul (KR); Hee Sup Shin, Uiwang-si (KR); Kyoo Bin Lee, Daejeon-si (KR)

(73) Assignee: Korea Institute of Science and Technology, Seoul (KR)

( * ) Notice: Subject to any disclaimer, the term of this patent is extended or adjusted under 35 U.S.C. 154(b) by 665 days.

(21) Appl. No.: 12/508,806

(22) Filed: Jul. 24, 2009

(65) Prior Publication Data
US 2010/0217351 A1 Aug. 26, 2010

(30) Foreign Application Priority Data
Feb. 23, 2009 (KR) .................. 10-2009-0014735

(51) Int. Cl.
*A61N 1/00* (2006.01)
(52) U.S. Cl.
USPC ............... 607/53; 607/54; 607/141; 607/152
(58) Field of Classification Search
USPC ..................... 607/53, 54, 141, 152
See application file for complete search history.

(56) References Cited

U.S. PATENT DOCUMENTS

| | | | | |
|---|---|---|---|---|
| 5,814,008 A * | 9/1998 | Chen et al. | ............ | 604/21 |
| 6,091,015 A * | 7/2000 | del Valle et al. | ............ | 136/243 |
| 6,711,440 B2 * | 3/2004 | Deal et al. | ............ | 607/9 |
| 2003/0004546 A1 * | 1/2003 | Casey | ............ | 607/1 |
| 2005/0278003 A1 * | 12/2005 | Feldman | ............ | 607/88 |
| 2006/0085051 A1 * | 4/2006 | Fritsch | ............ | 607/61 |
| 2007/0142877 A1 * | 6/2007 | McLean | ............ | 607/54 |

FOREIGN PATENT DOCUMENTS

| | | |
|---|---|---|
| KR | 10-2006-0010145 A | 2/2006 |
| KR | 2007-050258 A | 3/2007 |

OTHER PUBLICATIONS

Office Action dated Jan. 6, 2011 corresponding to the Korean Patent Application No. 10-2009-0014735 (w/translation).

* cited by examiner

*Primary Examiner* — Christopher D Koharski
*Assistant Examiner* — Natasha Patel
(74) *Attorney, Agent, or Firm* — Ohlandt, Greeley, Ruggiero and Perle, L.L.P.

(57) ABSTRACT

Disclosed is an apparatus for stimulating living body including a light source unit which irradiates an optical signal for generating an electrical signal; a photovoltaic cell unit which generates an electrical signal using a received optical signal; and an electrode unit which stimulates living body using the electrical signal, wherein the photovoltaic cell unit and the electrode unit are implanted in the living body. The apparatus for stimulating living body may be manufactured in a flexible form, so that it may extend the range of choice for site to be implanted for the apparatus. Further, the adoption of the photovoltaic cell unit avoids the need of surgical operation for the change of battery.

7 Claims, 8 Drawing Sheets

APPARATUS FOR STIMULATING LIVING BODY

CROSS-REFERENCE TO RELATED APPLICATION

This application claims priority to Korean Patent Application No. 10-2009-0014735, filed on Feb. 23, 2009, and claims all the benefits accruing therefrom under 35 U.S.C. §119. Korean Patent Application No. 10-2009-0014735 is herein incorporated by reference in its entirety.

BACKGROUND

1. Field

This disclosure relates to an apparatus for stimulating living body, which generates a stimulation signal with an optical signal. The apparatus for stimulating living body may be manufactured to be easily implanted in living body and may be operated for a long period of time because no battery is required.

2. Description of the Related Art

Typical electrical nerve stimulation devices include a deep brain stimulator (DBS) for patients with Parkinson's disease, a vagus nerve stimulator (VNS) for patients with epilepsy, and a spinal cord stimulator (SCS) for patients with chronic pain.

FIG. 1 shows a spinal cord stimulator according to the background art implanted in living body. A pulse generator is implanted above the ilium of a user, and an electrode is implanted at the stimulation site, i.e. the spine. The pulse generator and the electrode are connected with a wire and stimulate the spinal nerve. Since the spinal cord stimulator in the background art is a device having an electrode attached to the spine and having an electrical stimulator implanted above the ilium of a user and that requires a battery, it cannot be operated permanently. That is, surgical operation for the change of battery is needed once in about 5 years.

Recently, a spinal cord stimulator adopting a rechargeable battery was developed. It measures about 1 cm in thickness and about 3 cm in diameter, and is operable for about 10 years. However, it still requires surgical operation for the change of the battery. Accordingly, there is a need of a stimulation device with long operation life and easily implantable in living body.

BRIEF SUMMARY OF THE INVENTION

In order to solve the problems of the background art, there is provided an apparatus for stimulating living body, the implanted portion is manufactured to be flexible, so that it may be implanted at various sites, be implanted easily in living body, and more than one of them may be implanted at once.

The apparatus for stimulating living body includes a light source unit which irradiates an optical signal for generating an electrical signal; a photovoltaic cell unit which generates an electrical signal using a received optical signal; and an electrode unit which stimulates living body using the electrical signal.

The apparatus for stimulating living body may be manufactured to be flexible, so that it may be implanted at various sites. Since it may be implanted at various sites in living body, more than one may be implanted at once.

Further, surgical operation for the changing of the battery is unnecessary, because a photovoltaic cell is used instead of general battery.

It is also possible to allow a patient to control voltage through radio frequency (RF) transmission.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION OF THE INVENTION

Figure 1:
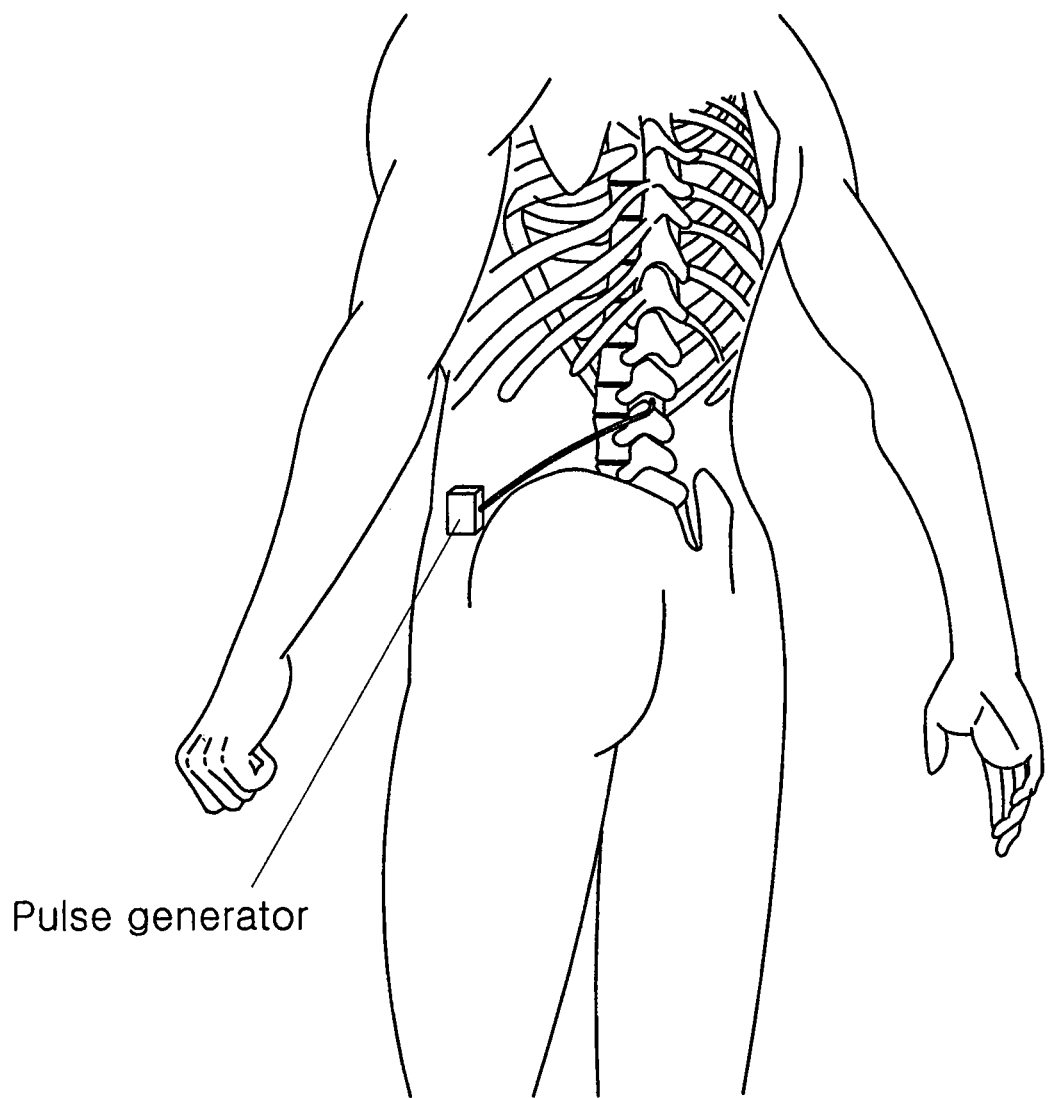
FIG. 1 is an apparatus for stimulating living body according to the background art implanted in human body.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Figure 2:
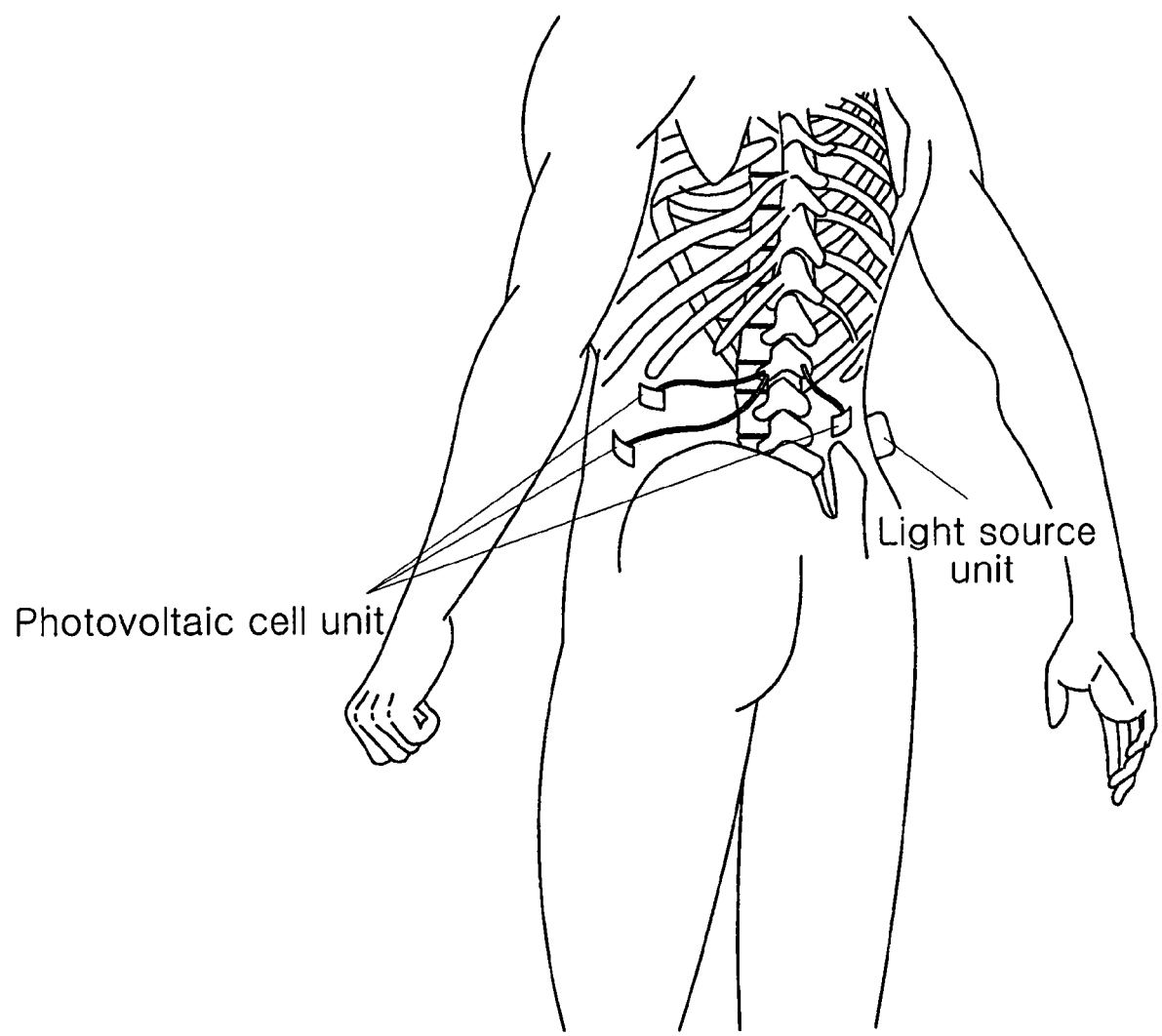
FIG. 2 shows an apparatus for stimulating living body according to this disclosure, implanted in a human body.

FIG. 2 shows an apparatus for stimulating living body according to this disclosure implanted in human body.

A photovoltaic cell unit which generates power after receiving an optical signal is implanted under the subcutaneous layer and is connected via wire to an electrode unit attached to the nerve. As used herein, the optical signal means a signal that can pass through the skin of living body. Hereinafter, a description will be made about an infrared (IR) signal among many possible optical signals.

When a portable light source unit applies a pulse of IR light (100 Hz, 100 μs (microseconds)) on the photovoltaic cell unit, therapeutic effect is attained through high frequency electrical stimulation (HFS) of the nerve. Here, 'on the photovoltaic cell unit' means the location where the optical signal of the light source unit can reach.

The photovoltaic cell unit is a device for generating an electrical stimulation and uses a photovoltaic cell. The photovoltaic cell is mounted on a flexible substrate. The photovoltaic cell unit and the electrode unit connected thereto are implanted in living body. The use of a photovoltaic cell instead of a general battery enables the photovoltaic cell unit to be implanted on a flexible substrate. Accordingly, the apparatus for stimulating living body of this disclosure may minimize burden during and after implantation into living body. The apparatus may be made to have a weight not more than 1 g and a volume more than 100 mm$^3$ (cubic mm).

Since the external portable light source unit is used as an operation power source, the photovoltaic cell may be made small, without a power source or a controller. Hence, since the photovoltaic cell unit is flexible and may be made small without the need of implanting a circuit for power control as used in the background art, the apparatus for stimulating living body of this disclosure may decrease the limit of the site to be implanted in living body. Further, the case when the photovoltaic cell is used provides a longer operation life than the case when the general batteries are used.

The photovoltaic cell unit generates electricity by receiving light. Typically, it has an operation life of 25 years and may be prepared to generate a voltage of 10 V (Volts) or more.

What is important with regard to stimulating of electricity to the nerve is that nearby nerve cells should be activated. It is known that pulse-type current, rather than direct current, activates the nerve cells in the brain. Important parameters include pulse intensity, duration and frequency. The portable light source unit is a device for emitting a pulse signal through an IR-emitting LED. When IR from the portable light source is irradiated to the photovoltaic cell unit, a pulse-type electrical signal may be generated. Accordingly, the pulse-type electrical signal may be applied to the nerve.

Physically the technology of converting light into current utilizes the photoelectric effect. Semiconductor devices such as photodiode, phototransistor, photovoltaic cell, etc., have been developed and are widely used in the manufacture of solar cells, cameras, or the like. It is also possible to manufacture a semiconductor that operates specifically depending on the wavelength of light. Among them, the photovoltaic cell and the photodiode operate under the same principle. They have the property of converting light into electricity and, thus, are used for solar power generation. If the photovoltaic cell is made to respond to IR (700 to 1100 nanometer) specifically, by equipping the photovoltaic cell with a filter, it is possible to make the photovoltaic cell generate an electrical signal using IR only.

As the light source for irradiating light to the photovoltaic cell, a light-emitting diode (LED), laser, etc. may be used. The LED operates at low voltage and current, and its optical characteristics are unharmful to living body in general. Also, due to high operation speed, it operates well even with high-frequency pulses of dozens of kHz. Among the commercialized IR LEDs, there is one capable of generating electricity in a photovoltaic cell at a distance of about 25 cm, with a rise time of about 2 μs (microseconds) and a radiant flux of 15 mW (milliwatts).

To conclude, an IR-emitting LED module is approached to the photovoltaic cell unit (equipped with an IR filter) implanted under the subcutaneous layer and a pulse-type optical signal is irradiated, so that the photovoltaic cell unit generates a pulse current and applies HFS to the nerve via an electrode, thereby attaining a therapeutic effect.

Figure 3:
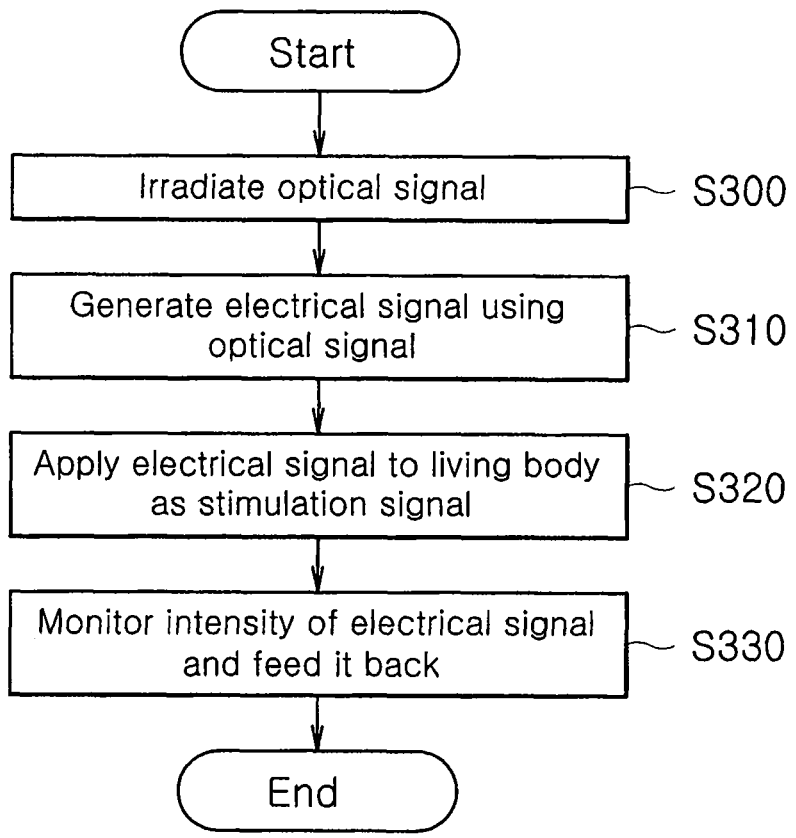
FIG. 3 is a flow chart illustrating the operation of an apparatus for stimulating living body according to this disclosure.

FIG. 3 is a flow chart illustrating the operation of an apparatus for stimulating living body according to this disclosure. The apparatus for stimulating living body operates as follows. At step S300, light source unit irradiates an optical signal for operating a photovoltaic cell unit. At step S310, a photovoltaic cell of the photovoltaic cell unit generates an electrical signal using the optical signal. At step S320, the generated electrical signal is applied to living body using an electrode. At step S330, the intensity of the electrical signal is monitored and the corresponding information is fed back to the light source unit. The feedback of step S330 is accomplished as follows. The voltage generated by the photovoltaic cell is detected and transmitted from the photovoltaic cell unit to the light source unit. After receiving the information, the light source unit adjusts the intensity of optical signal to correspond to the desired intensity of electrical signal for input and controls the intensity of optical signal. Further, the voltage generated by the photovoltaic cell may be detected and displayed, so that a user (a patient who had the apparatus for stimulating living body implanted) may see through a display unit.

Figure 4:
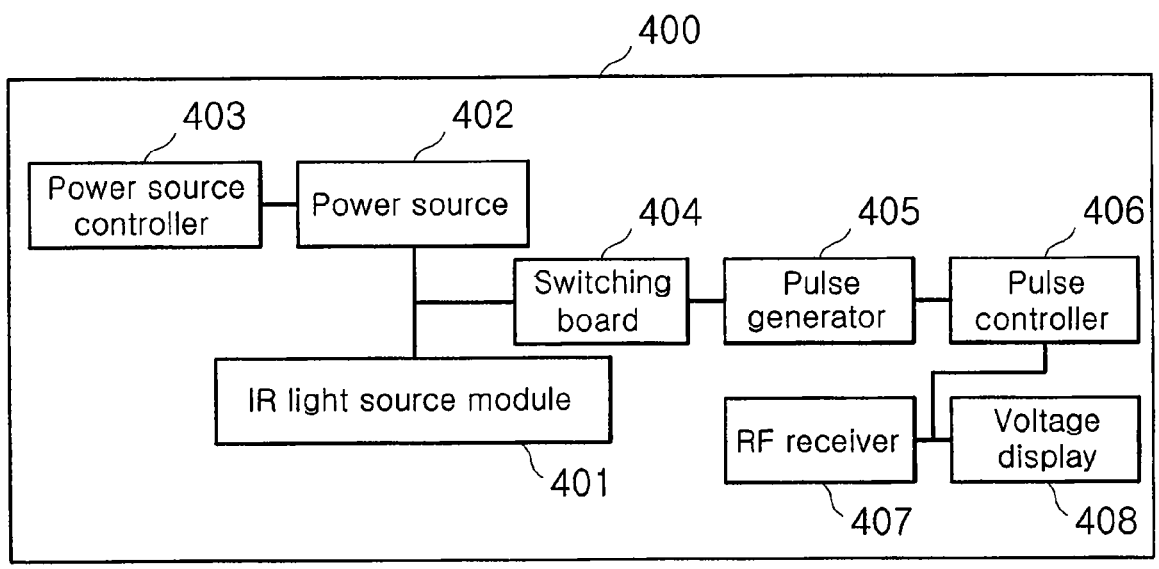
FIG. 4 is a block diagram illustrating the light source unit of an apparatus for stimulating living body according to this disclosure.

FIG. 4 is a block diagram illustrating the light source unit 400 of an apparatus for stimulating living body according to this disclosure. Herein, a description will be made about an IR signal among many possible optical signals. The light source unit 400 may comprise an IR light source module 401 which irradiates IR; a power source 402 which supplies power to light source unit 400; a power source controller 403 which controls power source 402; a switching board 404 which performs switching of power source 402; a pulse generator 405 which controls on/off of power source 402; and a pulse controller 406 which controls pulse generator 405. Further, pulse controller 406 may comprise a radio frequency (RF) receiver 407 which receives the data about the intensity of the voltage generated by the photovoltaic cell in the photovoltaic cell unit (FIG. 2); and a voltage display 408 which displays the data received by the RF receiver.

Figure 5A:
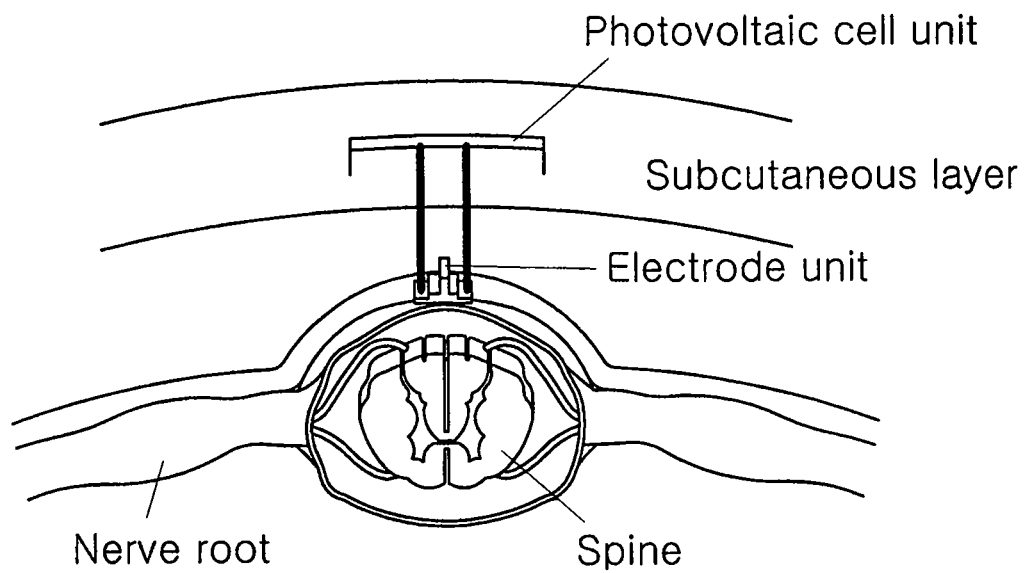
FIGS. 5a, b and c show the photovoltaic cell unit and electrode unit of an apparatus for stimulating living body according to this disclosure.
Figure 5B:
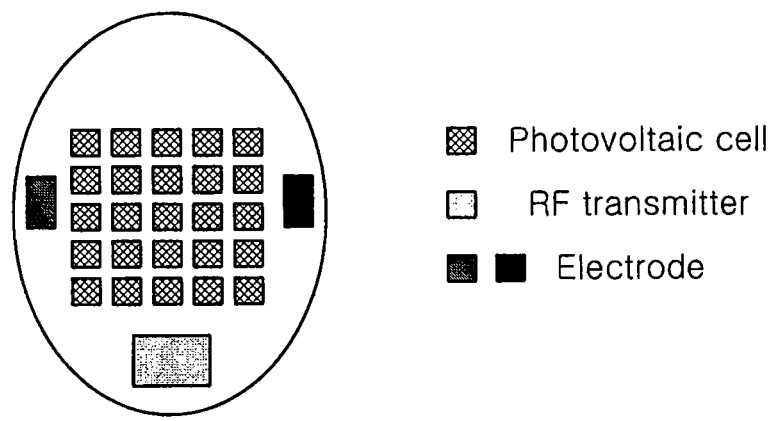
Figure 5C:
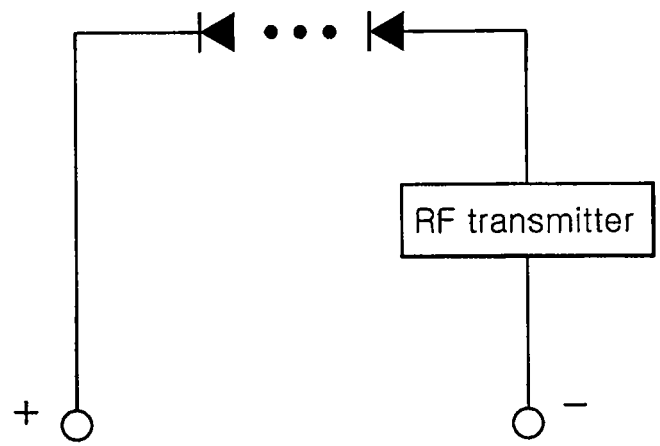

FIGS. 5(a), (b) and (c) show the photovoltaic cell unit and electrode unit of an apparatus for stimulating living body according to this disclosure. FIG. 5(a) shows the photovoltaic cell unit and electrode unit implanted in living body. The photovoltaic cell unit is implanted under the subcutaneous layer of living body and is connected via wire to the electrode unit attached to the spinal nerve. FIG. 5(b) shows the configuration of the photovoltaic cell unit and electrode unit. The photovoltaic cell unit may comprise a photovoltaic cell which generates an electrical signal using an optical signal; and an RF transmitter which transmits information about the intensity of the electrical signal to the light source unit. The electrode unit is attached to the spinal nerve and applies thereto the electrical signal generated by the photovoltaic cell unit. FIG. 5(c) shows a circuit diagram of the photovoltaic cell unit.

Figure 6:
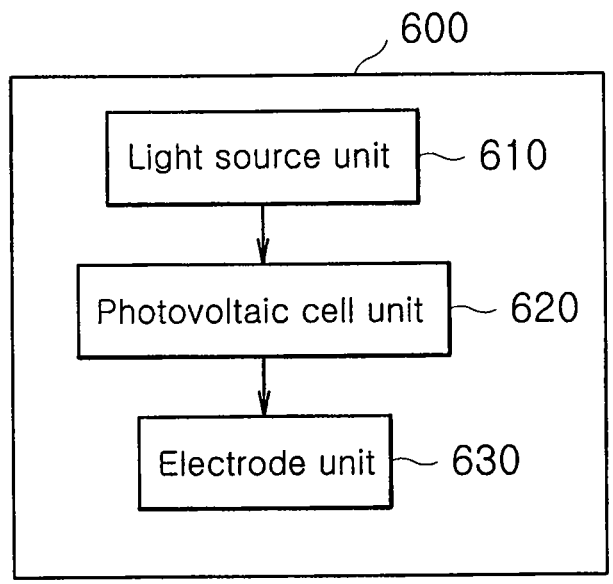
FIG. 6 is a block diagram illustrating an apparatus for stimulating living body according to this disclosure.

FIG. 6 is a block diagram illustrating an apparatus 600 for stimulating living body. Apparatus 600 may include a light source unit 610 which irradiates an optical signal for generating an electrical signal; a photovoltaic cell unit 620 which generates an electrical signal using a received optical signal; and an electrode unit 630 which stimulates living body using the electrical signal.

Light source unit 610 comprises an IR LED. One or more of intensity and frequency of the IR signal output from the IR LED may be controlled. Light source unit 610 may further comprise an RF receiver. The RF receiver may receive information about the intensity of the electrical stimulation. Light source unit 610 may be manufactured in the form of a band that can be attached to the skin of a user. When a plurality of photovoltaic cell units are implanted in the living body, the band-type light source unit may be attached at a site in which stimulation is desired to be applied. Then, an electrical stimulation may be applied by activating the corresponding photovoltaic cell unit. It is also possible to apply electrical stimulations at once at several sites by attaching a plurality of band-type light source units.

Photovoltaic cell unit 620 may comprise a photovoltaic cell which generates an electrical signal using a received optical signal. Further, it may comprise an RF transmitter which transmits information about the intensity of the electrical signal to the light source unit. The photovoltaic cell unit may be manufactured as a flexible film, so that it may eliminate the limit of site to be implanted in the living body, differently from the existing spinal cord stimulator.

Light source unit 610 is a device for operating the photovoltaic cell unit and that irradiates IR. A light source module may be assembled to manufacture a light source unit capable of creating a light field with desired area. Light source unit 610 is operated as connected with a power source. A pulse generator and a switching board control on/off of the light source unit. The RF receiver receives information about the intensity of the electrical signal transmitted by the photovoltaic cell unit and controls the power source to adjust the intensity of IR. Therefore, the user (patient) may control the voltage as desired.

Photovoltaic cell unit 620 is a device which substantially applies the voltage and is connected to the nerve via an electrode. Since a battery is not mounted thereto, it may be manufactured in the form of a flexible film. When the activation of a photovoltaic cell is about 1 mm, by serially connecting about 25 photovoltaic cells, a voltage of about 10 V may be obtained. The information about the generated voltage may be transmitted to light source unit 610 through the RF transmitter, so that the intensity of IR which is irradiated may be adjusted to generate an adequate voltage. Since photovoltaic cell unit 620 is small-sized and flexible, it may extend the range of choice for the site to be implanted.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. An apparatus for stimulating a living body comprising:
   a light source unit which irradiates a pulse-type optical signal for generating a pulse-type electrical signal;
   a photovoltaic cell unit which generates the pulse-type electrical signal using the pulse-type optical signal; and
   an electrode unit which is electrically connected to the photovoltaic cell unit, the electrode unit receives the pulse-type electrical signal directly from the photovoltaic cell unit and stimulates the living body using the pulse-type electrical signal,
   wherein the photovoltaic cell unit transmits information about an intensity of the pulse-type electrical signal to the light source unit, and
   wherein the light source unit receives the information about the intensity of the pulse-type electrical signal from the photovoltaic cell unit and controls an intensity of the pulse-type optical signal based on the intensity of the pulse-type electrical signal.

2. The apparatus for stimulating a living body according to claim 1, wherein the pulse-type optical signal is an infrared (IR) signal.

3. The apparatus for stimulating a living body according to claim 2, wherein the light source unit comprises an IR light-emitting diode (LED) and wherein the IR light-emitting diode emits the pulse-type optical signal, and wherein one or more of an intensity and a frequency of the pulse-type optical signal are controlled by the light source unit.

4. The apparatus for stimulating a living body according to claim 1, wherein the light source unit comprises a radio frequency (RF) receiver which receives the information about the intensity of the pulse-type electrical signal.

5. The apparatus for stimulating a living body according to claim 4, wherein the photovoltaic cell unit comprises an RF transmitter which transmits the information about the intensity of the pulse-type electrical signal to the light source unit.

6. The apparatus for stimulating a living body according to claim 1, wherein the light source unit is a band attachable to the skin of a user.

7. The apparatus for stimulating living body according to claim 1, wherein the photovoltaic cell unit is a flexible film.

* * * * *